US011380420B1

(12) United States Patent
Russo et al.

(10) Patent No.: US 11,380,420 B1
(45) Date of Patent: Jul. 5, 2022

(54) DATA STRUCTURE, COMPILATION SERVICE, AND GRAPHICAL USER INTERFACE FOR RAPID SIMULATION GENERATION

(71) Applicant: X Development LLC, Mountain View, CA (US)

(72) Inventors: Frank Russo, Sunnyvale, CA (US); Jason Thompson, Redwood City, CA (US); Nicholas Casavant, Palo Alto, CA (US); Yu Tanouchi, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 1095 days.

(21) Appl. No.: 15/973,415

(22) Filed: May 7, 2018

(51) Int. Cl.
| | | |
|---|---|---|
| *G06F 3/0484* | (2022.01) | |
| *G16B 5/00* | (2019.01) | |
| *G06F 8/41* | (2018.01) | |
| *G06N 5/02* | (2006.01) | |
| *G16B 45/00* | (2019.01) | |
| *G06F 3/04847* | (2022.01) | |

(52) U.S. Cl.
CPC ............ *G16B 5/00* (2019.02); *G06F 8/41* (2013.01); *G06N 5/02* (2013.01); *G16B 45/00* (2019.02); *G06F 3/04847* (2013.01)

(58) Field of Classification Search
CPC .......... G06F 8/41; G06F 3/04847; G06N 5/02
See application file for complete search history.

(56) References Cited

U.S. PATENT DOCUMENTS

| | | | |
|---|---|---|---|
| 2004/0029149 A1* | 2/2004 | Palsson | G16B 5/00 435/6.14 |
| 2004/0088116 A1* | 5/2004 | Khalil | G16B 50/20 703/11 |
| 2005/0171746 A1* | 8/2005 | Thalhammer-Reyero | G05B 17/02 703/2 |
| 2007/0005317 A1* | 1/2007 | Paxson | G05B 17/02 703/11 |

(Continued)

FOREIGN PATENT DOCUMENTS

WO   WO 2014/015196 A2   1/2014

*Primary Examiner* — Phenuel S Salomon
(74) *Attorney, Agent, or Firm* — Kilpatrick Townsend & Stockton LLP (57) ABSTRACT

A system is described for constructing a biological simulation using inputs from a knowledge base data structure and one or more templates. The knowledge base data structure comprises a set of entries representing distinct molecules and chemical reactions specific within the cell. Each template defines a sub-model program specification and a set of sub-model parameters to further characterize the sub-model specification. A graphical user interface is presented on a display for a user to view and select a templates and to assign information from the knowledge base to the selected template. From the graphical user interface, the user selects multiple templates to be included in the simulation and information from the knowledge base generally describing the cell. Based on the information selected from the graphical user interface, a compiler generates a simulation configuration data file comprising computer code capable of being executed by a simulation engine.

23 Claims, 7 Drawing Sheets

Example Working File
400

(56) References Cited

U.S. PATENT DOCUMENTS

| | | | |
|---|---|---|---|
| 2007/0250299 A1* | 10/2007 | Paxson | G16B 45/00 703/11 |
| 2008/0281864 A1* | 11/2008 | Itai | G16B 50/10 |
| 2009/0313189 A1* | 12/2009 | Sun | G16B 5/00 706/46 |
| 2011/0054654 A1* | 3/2011 | Phillips | G16B 50/00 700/98 |
| 2014/0019404 A1* | 1/2014 | Cho | G06N 5/022 706/59 |
| 2019/0136229 A1* | 5/2019 | Josephs | G16B 15/30 |

* cited by examiner

Example Working File 400

Working File Builder Interface 700

DATA STRUCTURE, COMPILATION SERVICE, AND GRAPHICAL USER INTERFACE FOR RAPID SIMULATION GENERATION

BACKGROUND

Field of Art

This description generally relates to data structures for use in simulation processing, graphical user interfaces for data structure construction, and computer service processes for data compilation.

Description of the Related Art

A simulation system may perform an experiment which runs one or more simulations on a model system of a cell, wherein each simulation has several simulation parameters. Simulation parameters may include reactants, amount of reactants, gene mutation, gene knockout, timing, availability of enzymes, etc. The result of each simulation is simulation data which describes the cell's state throughout the simulation. The model cell's state may comprise amount of molecules, reaction rates, and so on.

Computer data files may store all manner of information. Conventional computer simulation systems such as MATLAB and SCIKIT LEARN may specify generic data structures that handle different types of data such as vectors and arrays of training data. While flexible, this requires the operator to design a simulation entirely from first principles, harnessing together different datasets and logical operations together to craft bespoke simulations one at a time.

Due to the lack of a codified schema, the rapid construction of many simulations is hindered, which prevents operators from being able to, among other things, quickly design and run many similar simulations, or to quickly generate new, complex simulations that mix and match from different constituent parts. Existing approaches to this problem are often time-consuming, inefficient, and often results in inconsistently designed experiments.

SUMMARY

This description provides techniques for structuring and efficiently building configuration data files to be used for simulating the effects of changes in the biochemical reactions occurring within a cell.

A computer system provides a graphical user interface to receive instructions from a user to efficiently assemble and compile the simulation configuration file. The simulation configuration file can be built out of pre-constructed sub-model templates and parameters supplied as inputs to individual sub-files within a working data file which represents complete instructions for specifying how a cell model will be simulated. The coded instructions of the working data file are executed by a model compiler to generate the simulation configuration data file. Simulation configuration data files are further processed by a simulation engine to generate a simulated full model of a cell incorporating the cellular processes defined by the sub-files of the working data file.

Generally, these simulation configuration files are based on multiple sub-models each representing specific cellular processes. Cellular processes are defined using a combination of parameters including biological conditions, process characteristics, reactions, and molecules. Molecules represent specific inputs and outputs of the cellular processes and the reactions describe intermediary steps that take in input molecules and which produce output molecules. Biological conditions describe characteristics of the laboratory environment on which the simulated model is based. For each cellular process, process characteristics refer to quantities or classifications derived from primary data such as molecule amounts.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION OF DRAWINGS

I. Simulation Model of a Simulation System

Figure 1:
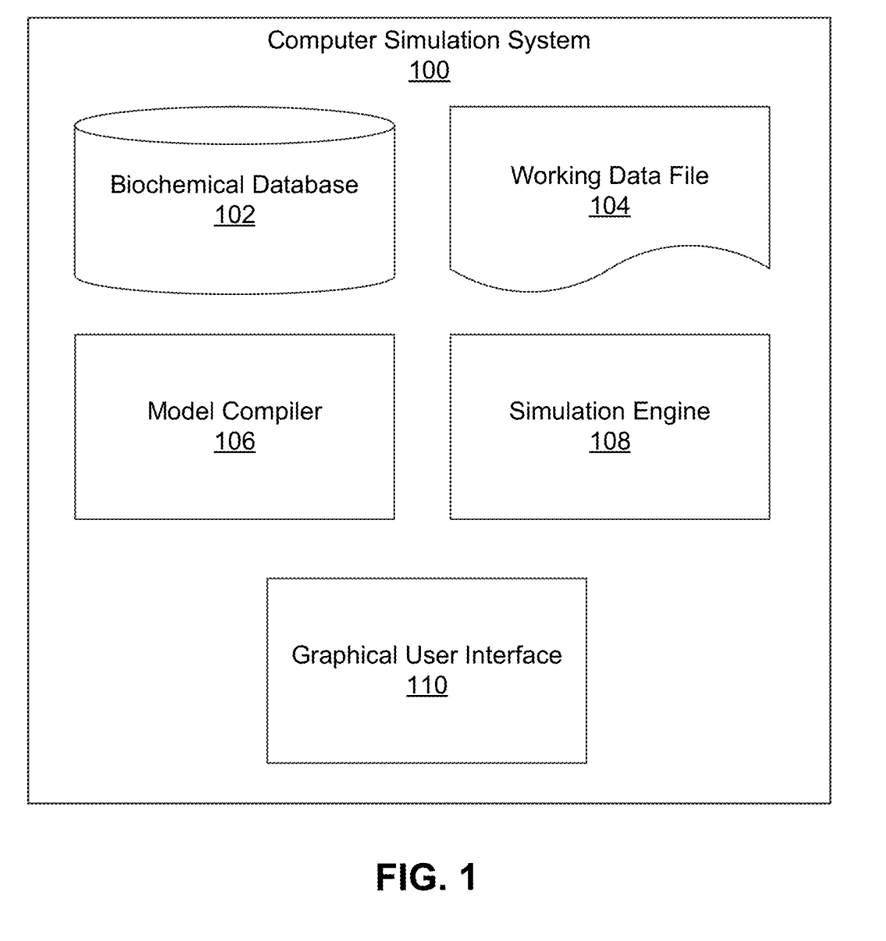
FIG. 1 is a block diagram illustrating computation components of a simulation system for modeling the behavior of a biological cell, in accordance with an embodiment.

FIG. 1 is a block diagram illustrating computational components of a computer simulation system 100 (herein referred to as simply "simulation system") for modeling the behavior of a biological cell, in accordance with an embodiment. Depending on the embodiment, each component of the simulation system 100 may implemented on one or more servers or other computational devices that are configured to communicate over a network (e.g. the Internet, a local area network, etc.). Alternatively, all computational components may be locally present on a single computational device. The computational components making up the simulation system 100 shown in FIG. 1 are a biochemical database 102, a working data file 104, a model compiler 106, a simulation engine 108, and a graphical user interface 110. The GUI 110 is described in further detail with reference to FIG. 6-7.

The biochemical database 102 is a database that stores data regarding molecules and processes that may be present or may occur in a biochemical environment simulated using the simulation system 100. The biochemical database 102 stores compositional data for each molecule that may be of use in the simulation, as well as data specifying how each molecule may be involved in one or more processes simulated by the simulation system 100. The biochemical database 102 may, more specifically, include information describing an organism at various levels of specificity. For example, on a more detailed level, the biochemical database 102 includes a catalog of an organism's genes, transcripts, proteins. At a higher level of generality, the biochemical database 102 may include structures such as an organism's protein complexes. Although any database structure may be used to implement the biochemical database 102, in one embodiment the biochemical database 102 is implemented as a bipartite reaction network 200 as described below in Section II. Those of skill in the art will recognize that the same biochemical information stored in the specified reaction network 200 could be stored in another type of database 102.

The working data file 104 (sometimes referred to as the working file) is a set of instructions for configuring the simulation system 100. The simulation system 100 may be configured to simulate a single set of molecules and processes and, therefore, is not configured separately for each use of simulation system 100. Alternately, the working file 104 is used to select the molecules and processes to be simulated in the simulation system 100, and is therefore configured separately for each use of the simulation system 100. Additionally, the working file 104 may designate the specific cell functions to be modelled as well as the models to be included in the simulation system 100. Furthermore, the working file 104 may include parameters for one or more submodels included in the simulation system 100, as well as a set of initial conditions for each of those models.

The model compiler 106 uses working file 104 to compile the simulation system 100 so that simulations can be run. The model compiler 106 accesses the data retrieved from the biochemical database 102 and the working file 104 to generate various components of each simulation, examples of which include but are not limited to: a stoichiometric matrix, a bipartite network link molecule and process nodes, initial flux vectors that describe the rate of production and/or consumption of molecules and quantities prior to a model being run for the first iteration, an objective function for each model, and any constraints on any of the models. After processing the various components of the simulation, the model compiler 106 outputs a simulation configuration data file (sometimes referred to as a configuration file or simconfig file). The configuration file is an input to the simulation engine 108 to generate a simulation of the cellular process described by the working file 104. In some implementations, the configuration file is a set of instructions to be executed by the simulation engine to accurately generate a simulation.

The simulation engine 108 manages the execution of the configuration of simconfig file produced by the model compiler 106 to simulate a biochemical process using the simulation system 100. The simulation engine 108 may initialize a given simulation using the initial conditions as constructed by the compiler 106 and as contained in the simconfig file. The simulation engine 108 creates an initial state vector, which includes the concentration of each molecule included in the simulation, which sets an initial rate of consumption and production for the associated molecules. The simulation engine 108 creates any initial exchange flux values into and out of each model in the simulation. The simulation engine 108 then iterates through a time step of the simulation, running the models of the simulation with the input state vectors and fluxes. Generally, this involves the simulation engine 108 arriving at a solution of the model for a first time step after the initial state, where the time step is of a predetermined length. The solution for each model for that time step may include, but is not limited to, the concentrations of the molecules output by each model, the fluxes of those molecules, and any changes to the overall biochemical environment (e.g. temperature changes, pH changes, etc.) caused by the processes being simulated by each model.

After the completion of the initial time step of the simulation, the simulation engine 108 updates the initial state vectors, flux vectors, and any other relevant state vectors with the output of the initial time step. As a specific example, the simulation engine 108 may use the fluxes determined during the running of the models multiplied by the length of the predetermined time step to determine the new concentrations of the molecules included in the models of the simulation. As another specific example, the simulation engine 108 may also calculate the exchange fluxes that connect each model with each other model in the simulation. The simulation system 100 then runs a second time step of the simulation similarly to the first time step using the updated state vectors and any other parameters of the simulation. The simulation engine 108 continues this process for a number of time steps or until reaching a termination state or receiving a termination input.

II. Biochemical Database

The biochemical database 102 stores a reaction network structured as a bipartite graph, according to one embodiment. A reaction network characterizes a reaction pathway, the inputs, and the outputs of any steps occurring along the reaction pathway. The bipartite graph consists of two distinct sets of nodes, molecule and process, which are connected by edges. A bipartite graph, additionally, includes input molecule nodes representing the input molecules of the reaction. Each of the input molecule nodes is connected to at least one of the intermediary, process node or an output molecule node by one or more edges.

Within a bipartite graph structuring of a reaction network, input molecule nodes represent the first products of the reaction. Depending on the number of molecule and process nodes in the pathways of the reaction network, there may be any number of additional molecule nodes and edges in the reaction network showing the reaction pathways from input molecule nodes to output molecule nodes. In one specific use of such a network, the output molecule nodes represent the outputs of a particular cell function (or set of cell functions) such as metabolism, and are the output boundary of the bipartite metabolic network 100.

A molecule node may represent small molecules such as water, carbon dioxide, protons, etc. or macromolecules such as proteins, lipids, alcohols, organic acids, vitamins, etc. A molecule node may also represent organism specific molecules such as transcripts, proteins, and protein complexes. A molecule node may contain a plurality of metadata fields to describe the molecule including the molecule name, a molecule formula, an amino acid sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories. In some examples, molecule nodes may have associated flux values. Flux values of molecule nodes represent a net rate of downstream consumption of the molecule and upstream production of a molecule. Flux values thus describe the "flow" of the molecule through a reaction network.

Process nodes describe molecular actions in a biochemical environment including but not limited to chemical reactions, regulatory interactions, binding, transport, or others. A process node includes a number of descriptive metadata fields that provide information about the process including but not limited to a list of molecules and their associated roles in the process, reaction rate information, and energy requirements for the process, sub-processes that may be involved in the process, or other more detailed information.

In alternate embodiments, the biochemical database 102 may store information describing cellular processes using a different representation from the bipartite representation example above. For example, a transcription sub-model modeling cell transcription may use transcripts and relative concentrations to construct a monomial distribution sampled at various time steps or sequence composition techniques to translate the sampled set of transcripts into an analysis of nucleoside triphosphate demand, for which a bipartite reaction network would be less useful than other representations.

III. Sub-Models in Cell Modeling

Figure 2:
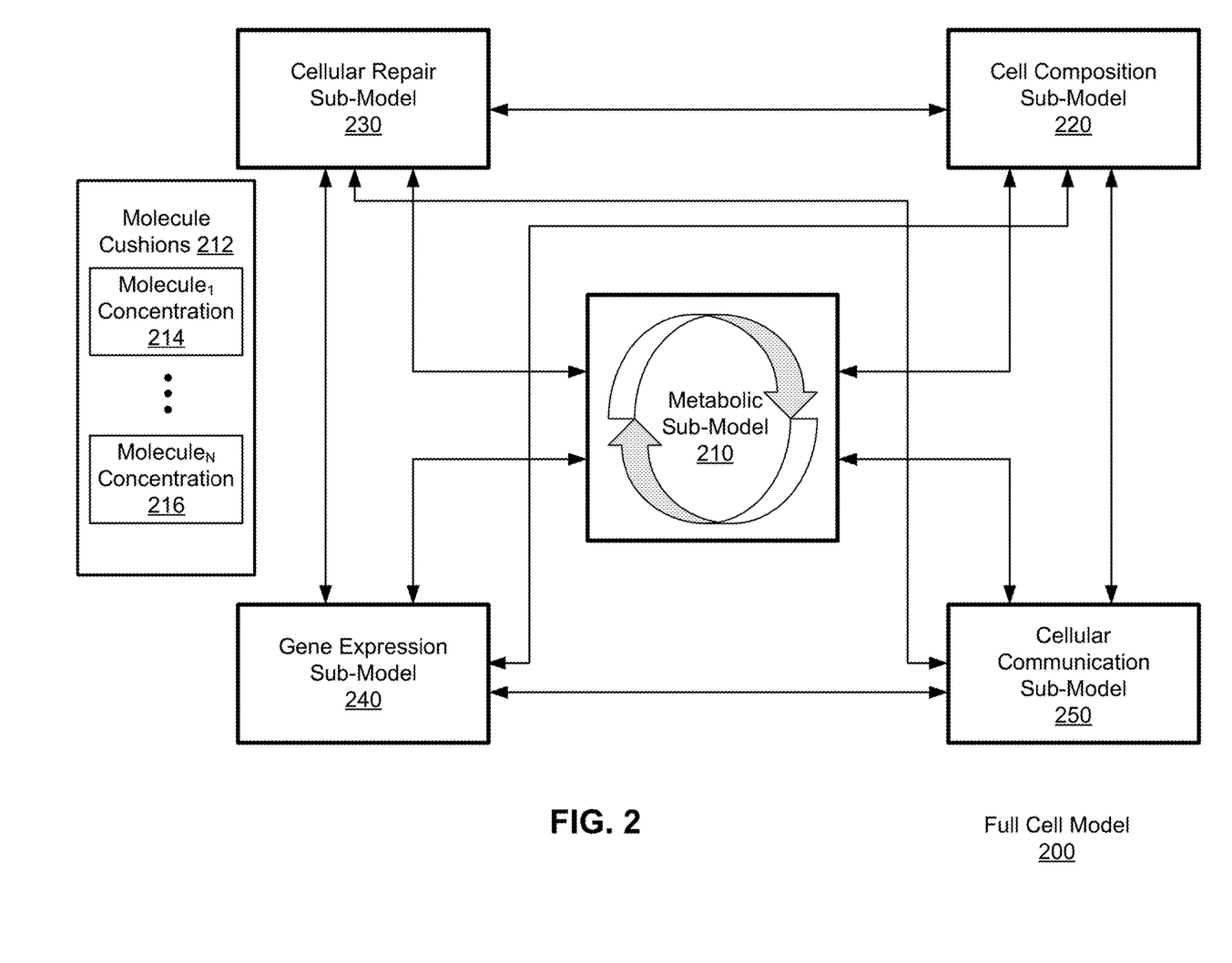
FIG. 2 is a block diagram illustrating a full cell model, according to an embodiment.

FIG. 2 is a block diagram of a full cell model 200, according to one embodiment. The full cell model 200 contains a cellular metabolic sub-model 210 with any number of sub-models which input and/or output with other sub-models or the cellular metabolic sub-model 210. The sub-models include the cellular repair sub-model 220, the cell composition sub-model 220, the gene expression sub-model 240, and/or the cellular communication sub-model 250. The arrows leading to the cellular metabolic sub-model 210 represent the input flux and/or output flux values between the cellular metabolic sub-model 210. Arrows between sub-models and cellular metabolic sub-model 210 may also represent the supply of molecules from these sub-models to cellular metabolic sub-model 210.

As shown in FIG. 2, arrows lead from sub-models into cellular metabolism 306 and from cellular metabolic sub-model 210 into sub-models. This is an illustration of the fact that many cellular processes contain molecules and reaction pathways that are both inputs into cellular metabolic sub-model 210 and which are produced by cellular metabolic sub-model 210. Thus the sub-models shown in FIG. 2 may be both upstream sub-models and downstream sub-models, as described with reference to FIG. 1. The interactions between sub-models and cellular metabolic sub-model 210 may be coordinated by a single dataset that aggregates changes within the full cell model 200, such that each of the sub-models and cellular metabolism 306 receive and transmit information to the single dataset, rather than to each other. This single dataset may be a state dataset, and is described in further detail with reference to FIG. 2.

In addition to molecule concentrations within sub-models and cellular metabolic sub-model 210, the full cell model 200 may include molecule cushions 212 that exist outside of system of supply and demand between the sub-models and cellular metabolic sub-model 210. The molecule cushions 212 represent reserves of molecules within the cellular environment. For example, molecule cushions 212 may be molecules that exist within a cell's cytoplasm, and which are available to molecular processes when needed. Molecule cushions 212 contain different reserve concentrations of different molecules. For example, a first molecule, molecule$_1$, may have a concentration molecule$_1$ concentration 214. If molecule$_1$ is a molecule that has a large flux value or demand within the system of sub-models and cellular metabolic sub-model 210, then the reserve concentration of molecule$_1$ may be larger than other molecules with smaller demand. Thus the concentration of molecules within molecule cushions 212 may be proportional to the flux value associated with the molecule in cellular metabolism, the aggregate demand for the molecule within the sub-models, and/or any other measurement of demand within the system of sub-models and cellular metabolic sub-model 210. The molecule cushions 212 ensure that sudden increases in demand for a molecule within the full cell model 200 do not result in complete depletions of a molecule within the full cell model 200.

There may be any number of molecules within molecule cushions 212. A total of N molecules, represented by molecule$_N$ concentration 214, are assigned reserve concentrations within molecule cushions 212. In some examples, all molecules within the full cell model 200 are assigned reserve concentrations within molecule cushions 212. In other examples, molecules with demand and/or flux values above a threshold are assigned reserve concentrations within molecule cushions 212, such that a subset of the molecules within the full cell model 200 representing the primary flow of molecules are stored in molecule concentrations molecule$_1$ concentration 214 through molecule$_N$ concentration 216.

The effect of the molecule cushions 212 on the full cell model 200 is that the molecule cushion concentrations allow the demand for a molecule to instantaneously (e.g., for a given single time step evaluating the subunits) exceed supply without disrupting the full cell model 200. This allows the production network to continue to function as a demand load is applied to the system of the full cell model 200, giving the cell time to increase production of the molecule to meet the new demand.

IV. Simulation Working File Data Structure

IV.A Sub-Model Templates

Figure 3:
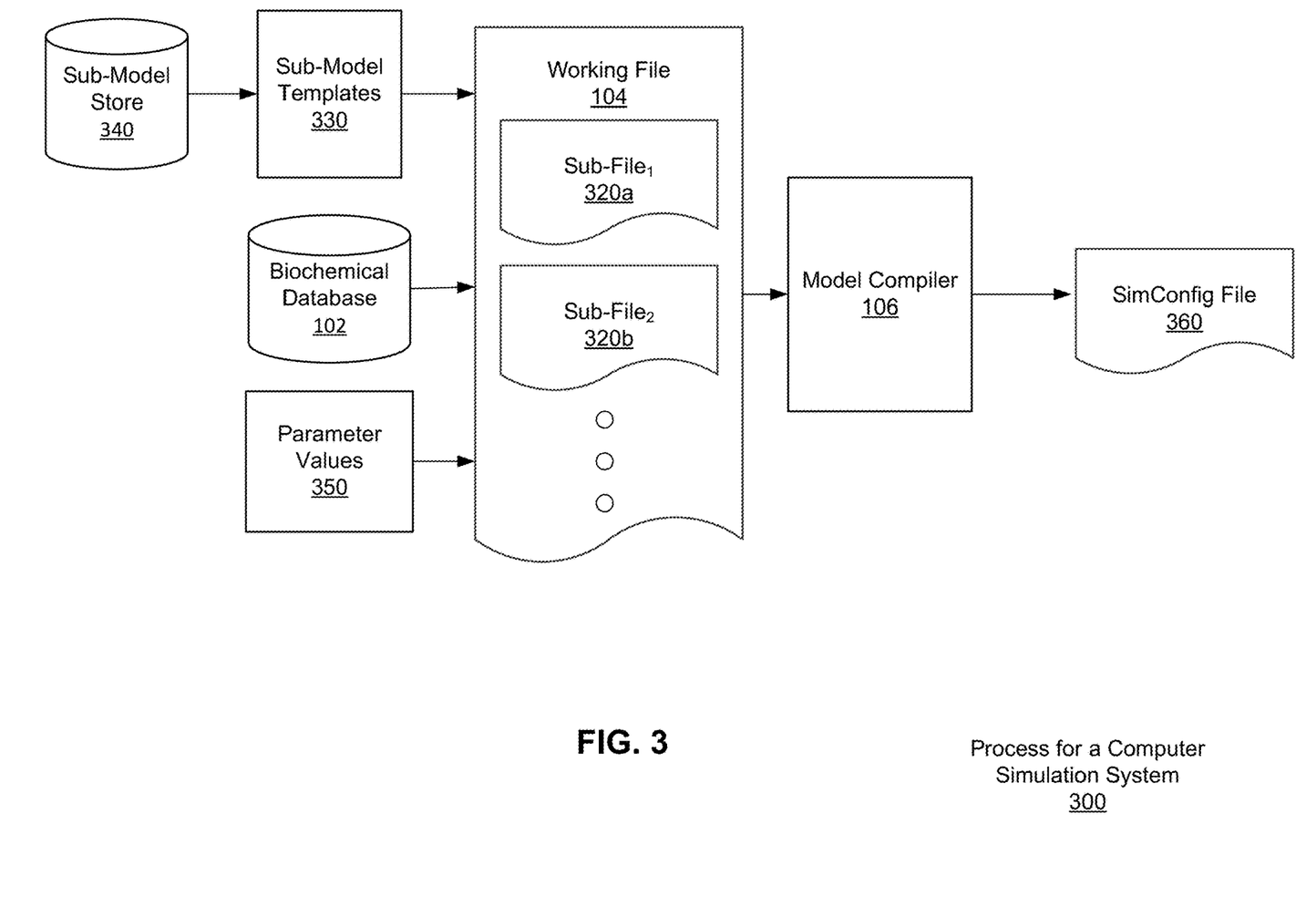
FIG. 3 is a flowchart illustrating the implementation used to construct a biological simulation, according to an embodiment.

FIG. 3 is a flowchart illustrating an example process for generating and compiling a working data file that may be compiled and used to run a cell simulation, according to an embodiment. Users interested in testing the effects of specific changes in intracellular conditions may have on the overall health of a cell design a simulation to model and interpret those effects in a more efficient and accurate method than conventional wet-lab techniques. Because intracellular changes affect cellular processes, which in turn determine whether a cell will lyse, a user must specify which cellular processes to include in the simulation of their experiment. For example, a user interested in understanding the effects of a specific modification in RNA transcription specifies that their simulation should include gene expression processes. Experiments of greater complexity may require the specification of cellular processes. In some implementations, cellular processes that are not modified by the user, but are still integral to healthy cell activity, are included in the system under default conditions. To that end, the simulation system 100 asks that users specify the required cellular processes by selected sub-models from the sub-model store 340.

As described above in reference to FIG. 2, sub-models are used to represent individual cellular processes occurring within a cell. As a result, the full cell model 200 generally incorporates multiple cellular processes, for example cellular repair, cell composition, cellular communication, and gene expression. The sub-model store 340 stores specifications for the aforementioned sub-models along with additional sub-models describing additional cellular processes. A sub-model specification includes an identifier indicating the nature and function of the process as well as sub-model parameters of information required to characterize the process. For example, the cellular repair sub-model may include sub-model parameters describing the concentration of intracellular ATP, an indication that the cell is undergoing glycogenolysis, or a change in intracellular pH. When accessed from the sub-model store 340, the sub-model specification is assigned to a template file. Based on the sub-model specification, the simulation system 100 dynamically reconfigures the template to feature the sub-model parameters such that relevant information can be assigned to the sub-model parameters. The reconfigured template is hereafter referred to as a sub-model template 330. The reconfiguration of the template into a sub-model template is performed automatically in response to the assignment of a sub-model specification to a template, by a user interacting the graphical user interface 110.

Once the simulation system has received the required sub-models from the user, the simulation system requests, by presentation of the graphical user interface 110, information from the user to characterize each of these cellular processes. More specifically, the simulation system requires information to describe both manipulated and controlled variables affecting each of the processes represented by a sub-model. For example, each cellular process requires a set of molecules to be used as reactants, each set of reactants follows a certain reaction network to yield a set of products, and each of these reactions may be affected by environmental conditions under which the experiment was conducted. As a result, an accurate and holistic simulation requires specification, received from the user, for each of these considerations to characterize experimental properties such as those mentioned above.

As described above in reference to FIG. 1, information stored in the biochemical database 102, referred to hereafter as "entries," describes potential cellular conditions. In one implementation, entries within the biochemical database 102 characterize the cell and its functionalities at a set of equilibrium or default conditions. Among other pieces of cellular information, the biochemical database 102 stores one or more reaction networks 200 detailing the input molecules 202 and output molecules 240 associated with the various cellular processes. Entries from the biochemical database 102 are accessed and assigned to one or more sub-model templates 330 to populate the sub-model parameter fields.

When assigned to one or more sub-model parameters, entries are referred to as "parameter values." Parameter values 350, individually or in combination, describe or provide context regarding one or more of the following parameter categories: laboratory conditions, experimental characteristics, reactions, and molecules. The selection of molecules to be included in a simulation is further described below.

Laboratory conditions refer to one or more of the following: an environmental temperature, a type of plating, or a set of atmospheric conditions. Experimental characteristics refer to one or more of the following: the quantity being measured by the simulation, for example a concentration of ATP, and a method for analyzing that quantity. Molecules refer to the one or more input molecules, one or more output molecules, and one or more reactions relating the input molecules to the output molecules.

As further examples, experimental characteristics for a metabolism sub-model with a flux balanced analysis sub-model specification may include a measurement of the total biomass based on levels of deoxynecluoside triphopsphatses, nucleoside triphosphates, amino acids, and other metabolites. The same metabolism sub-model may include specifications for molecules that representing input molecules with associated maximum influx rates and process molecules representing available medium components with associated exchange fluxes. Similarly, a model specified for a biomass sub-model may specify the molecules of interest to be monitored over time. Laboratory conditions for the same template may describe a set of default, specific flux balanced analysis parameters. The laboratory conditions for the template may be adjusted or modified based on user preferences for the simulation.

As additional examples, a template specified for a transcription sub-model may specify molecules involved in reactions converting nucleoside triphosphates into ribonucleic acids, a laboratory conditions describing the concentration of an enzymatic agent such as RNA polymerase, and an experimental characteristic describing the transcription rate of RNA per enzymatic agent. Similarly, a template specified for a translation sub-model may specify molecules involved in reactions converting amino acids into proteins, a laboratory condition describing a translation agents such as a ribosome, and an experimental characteristics describing the translation rate of amino acids per molecule of translation agent. Moreover, a template specified for a replication sub-model may specify molecules involved in reactions converting deoxynucleoside triphosphatases into DNA and an experimental characteristic describing the production rate of DNA.

In some implementations, the parameter values 350 are not based on entries accessed from the biochemical database. For example, parameter values 350 may be set to default parameter values based on standard conditions within a cell or conditions that a user has previously used in their simulations. Alternatively, parameter values 350 may be set manually by users of the computer simulation system. A graphical user interface 110 may be displayed on a computer screen to (among other tasks) receive, from a user, a selection of entries from the knowledge base and assign them to sub-model parameters. Similarly, the same graphical user interface 110 may receive instructions from a user to directly assign a parameter value 350 to a sub-model parameter field independent of the entries stored within the biochemical database 102. The graphical user interface is further described below in reference to FIGS. 6 and 7.

Parameter values 350 are not fixed entries based on the specification of the sub-model template 330 to which they are assigned. Two copies of a sub-model template receiving the same sub-model specification may be populated using different entries for each sub-model parameter field. For example, a cellular repair sub-model 230 may include a parameter field requesting information describing the level of ATP production. One copy of a cell repair sub-model 230 may receive a parameter value indicating a fully functional ATP pump while the second copy of the same sub-model indicates a failing ATP pump, resulting in post-simulation differences between the cellular repair processes. In another example, the cell composition sub-model 220 includes a sub-model parameter field for information regarding the concentration of $Na^+$ in the cell. One copy of a cell composition sub-model 220 may indicate a concentration of $Na^+$ above an equilibrium level, whereas a second copy of the cell-composition sub-model 220 may indicate a concentration below the equilibrium level. In either of the above examples, the results are simulations of two cells similar in some cellular processes, but differing in regards to processes associated with the manipulated parameter values 350.

IV.B Working File

After characterizing the cellular processes occurring within the cell by assigning a plurality of parameter values to each of the sub-model templates, the simulation system 100 generates a working file 104 prescribing a set of instructions for generating the simulation of the biological cell. In one implementation, illustrated and described further in reference to FIG. 6, one or more sub-model templates 330 are initially generated and populated with the required biological information and are selected for inclusion in the working file 104 for simulation of the specified cellular processes. Once incorporated into the working file 104, a sub-model template 330 is referred to as a sub-file 320. In the above implementation, the graphical user interface 110 would receive instructions from the user to incorporate the sub-model templates 330 into the working file 104 without further modifying the respective sub-file 320.

Figure 7:
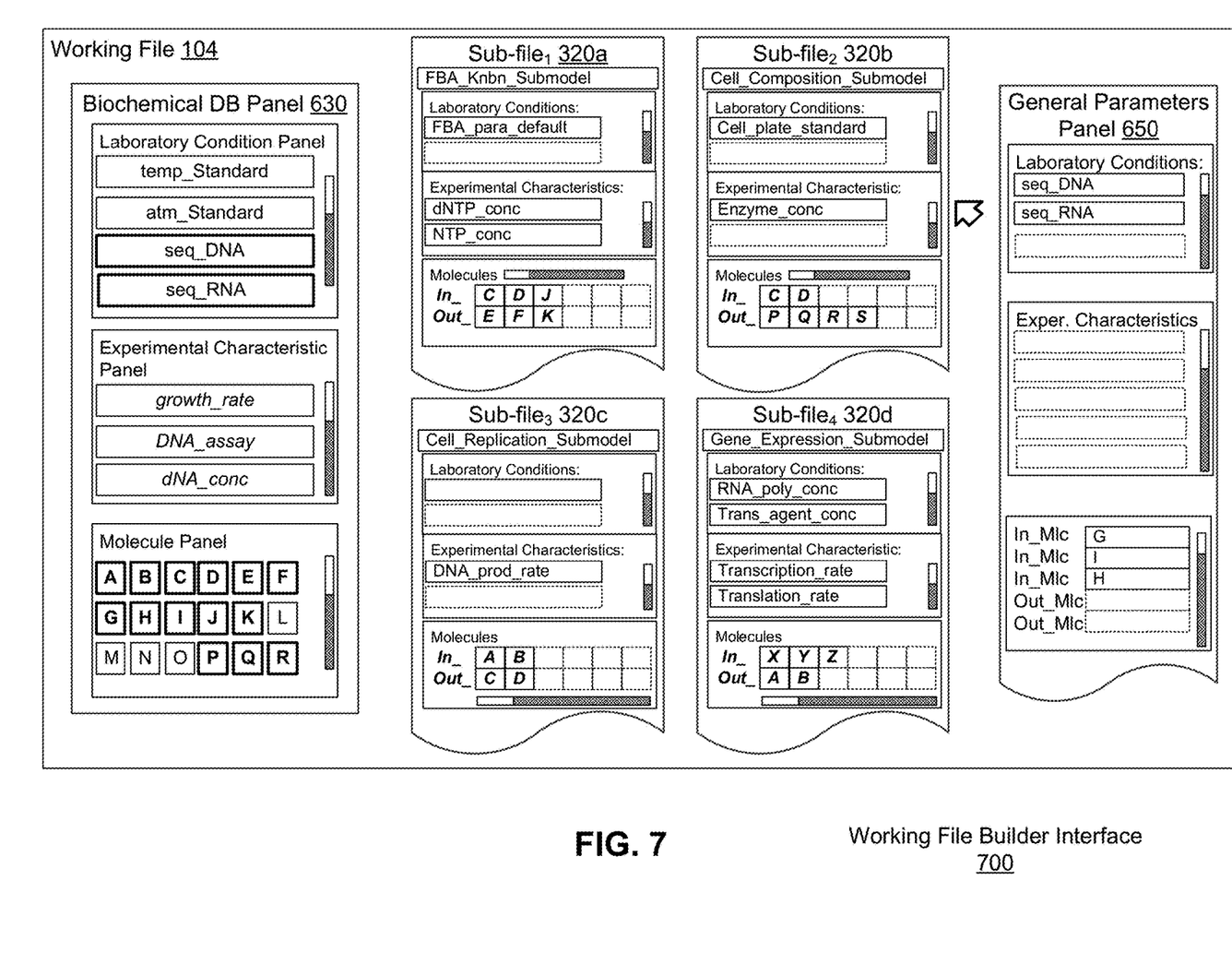
FIG. 7 is an illustration of an example graphical user interface for editing one or more sub-files as displayed on a computer screen, according to an embodiment.

In an alternate implementation, illustrated and described further in reference to FIG. 7, one or more existing sub-model templates 330, populated with the required biological information, are maintained by the simulation system 100 to be referenced in future simulations. For example, a user performing a second experiment using the same set of similar intracellular conditions, but manipulating a different set of parameters, may recall from the persistent memory of the simulation system the same set of sub-model templates 330 used in the first simulation and manually update the parameter values of interest. Similarly, if a user is only interested in replicating a single cellular process from a previous simulation, the simulation system only recalls a single sub-model template. In such an implementation, the graphical user interface 110 would not receive instructions from the user to generate a new sub-model template 330, but rather to modify a sub-file 320, which was based on an existing sub-model template 330.

Depending on the complexity and innovation of a simulation, a combination of the two implementations may be required. For example, the simulation system may recall one or more sub-model templates 330 for modification as sub-files 320 of the working file 104 while simultaneously generating new sub-model templates 330 to be included in the same working file 104. In such an example, the simulation system may alternate between two graphical user interfaces-one for the generation of new sub-model templates 330 and another for the modification of existing templates as sub-files 320. Such graphical user interfaces are further described below in reference to FIGS. 6 and 8.

Figure 4:
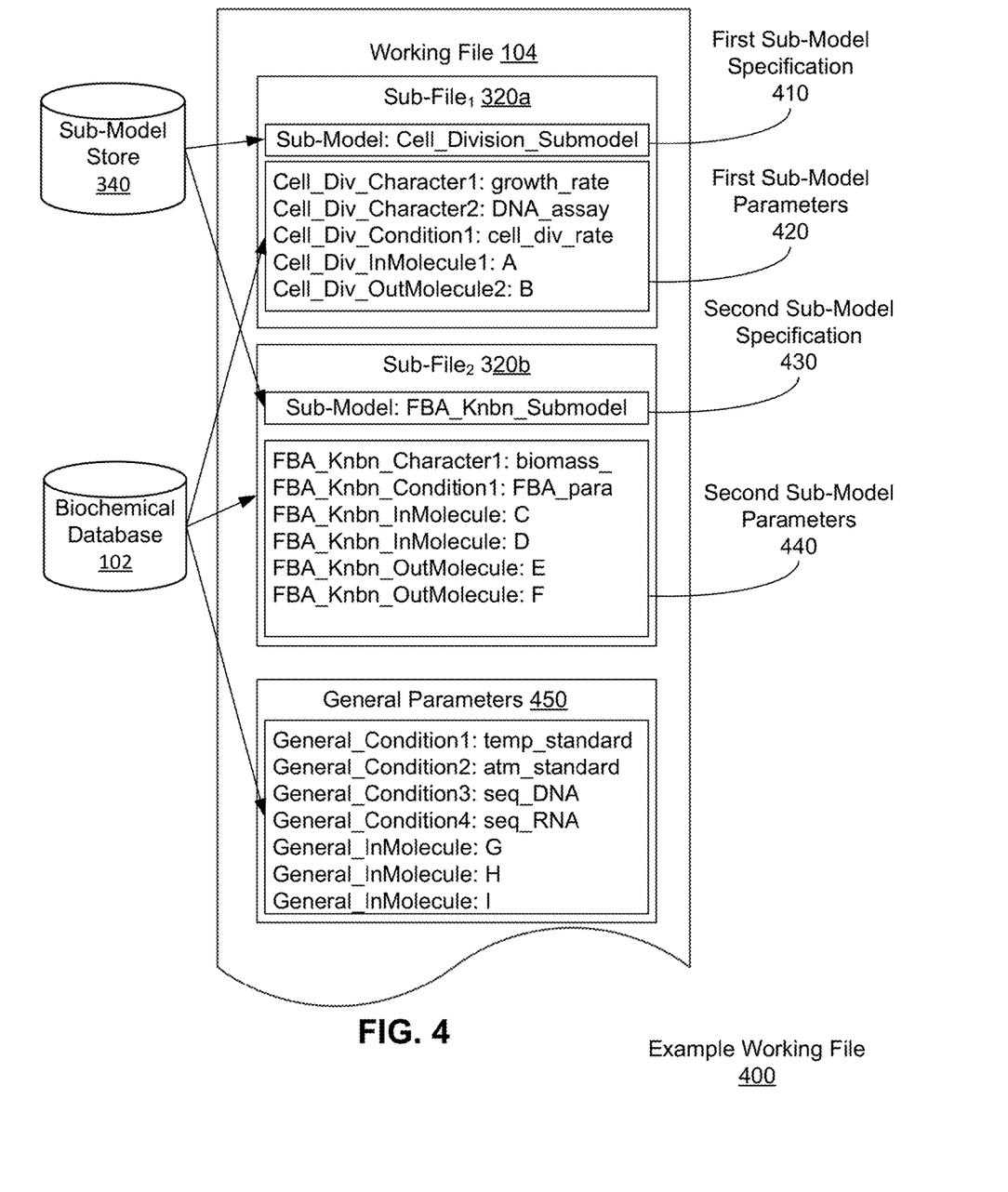
FIG. 4 is an illustration of an example working file, according to an embodiment.

To that end, a user may interact with the graphical user interface 110 to select sub-model templates 330 for inclusion in the working file 104 for simulation of biological cell processes. Once incorporated into the working file 104, sub-model templates 330 are referred to as sub-files 320. As illustrated in the example of FIG. 4, two sub-files: sub-file$_1$ 320a and sub-file$_2$ 320b are selected to be incorporated into a working file 104. The working file 104, ultimately inputted to the model compiler 106 to generate the simulation of the cell, includes identifiers for specific parameters values 350 stored within the biochemical database 102 that are used to generate the simulation.

In addition to the parameter values 350 associated with each of the sub-model templates 330, the graphical user interface 110 may also receive, from a user, a set of general parameters to be assigned to the working file 104. General parameters describe characteristics within the simulated cell that are: 1) a characteristic of the cell that is independent of any of the assigned sub-files 320 and 2) a characteristic of the cell that is shared between more than one of the assigned sub-files 320. For example, if all selected sub-files 320 share an input molecule 202, the input molecule may be stored within the working file 104 as a general parameter. Alternatively, that same input molecule 202 may not be specifically required by any of the sub-files 320, but be required generally for the basic functioning of the cell and is therefore stored as a general parameter.

Examples of parameters falling under the first category include, but are not limited to, general laboratory conditions, general experimental characteristics, and molecules within the cell. Examples of general laboratory conditions include, but are not limited to, the medium that the cell is grown in. Examples of general experimental characteristics include, but are not limited to, the DNA sequence of the organism, one or more edits to the DNA sequence for the organism, the RNA sequence for the organism, and one or more edits to the RNA sequence for the organism.

Referring now to FIG. 4, FIG. 4 illustrates an example of a working file 104 consistent with the description above. The working file 104 includes two sub-files with distinct sub-model specifications 410 and 430. Both sub-model specifications are accessed from the sub-model store 340. The first sub-file, Sub-File$_1$, describes cell division processes as indicated by the specification 410 "Cell_Division_Submodel." The first sub-model parameters 420, associated with Sub-Files 320a, include a combination of experimental characteristics defining the intended measurements associated with the experiment, laboratory conditions, and molecules. Specifically, the experimental characteristics (Cell_Div_Character1 and Cell_Div_Character2) include an analysis of the growth rate of cells on a plate (growth_rate) and a DNA assay (DNA_assay). Regarding molecules, A is a specified input molecule and B is a specified output molecule for the reaction represented by the cell division sub-model 320a.

The second sub-file, Sub-File2, characterizes processes associated with metabolic processes using Flux Balanced Analysis-based assumptions as indicated by the specification 430 "FBA_Knbn_Submodel." The second sub-model parameters 440, associated with Sub-Filet 320a, also include a combination of experimental characteristics, laboratory conditions, and process molecules. However, all of the specified parameters 440 differ from the parameters 420 specified for the first sub-model. Specifically a different set of laboratory conditions are specified to describe a set of default FBA parameters (FBA_para). Instead of input molecule A and output molecule B, C and D are specified as input molecules and E and F are specified as output molecules. Experimental conditions specific to the FBA sub-model 320b include a measure of the cells biomass based on the levels of the dNTP's, NTP's, and amino acids. Regarding the general parameters, general conditions are specified to define the laboratory environment for the simulated cell (General_Condition1, General_Condition2, General_Condition3, and General_Condition4) such as the temperature within the laboratory (temp_standard), atmospheric conditions within the laboratory (atm_standard), the DNA sequence (seq_DNA), and the RNA Sequence (seq_RNA). Additionally, G, H, and I are specified as input molecules. The parameter values defined for the parameters 420 and 440 are specified manually by a user or supplied as entries from the biochemical database 102.

Although not illustrated in FIG. 4, graphical user interface may also receive a set of reactions to relate the specific input and output molecules for each sub-file 320. In some implementations, a specification for a reaction includes a set of associated input molecules as reactants and output molecules as products. For example, a reaction associated with a metabolism sub-file describes glycolysis including one glucose molecule as an input molecule and two pyruvate molecules as output molecules. Alternatively, a reaction parameter is not explicitly selected as a parameter, but rather is implicitly selected based on the molecules selected as reactants and products for the simulation. Continuing from the glycolysis example, a selection of one glucose molecule as an input molecule and two pyruvate molecules as output molecules may indicate that the sub-file 320 implements a glycolysis reaction, without the reaction being a parameter selected by the user.

IV.C Model Compiler

After designing the experiment within the working file 104, the simulation system 100 allows the user test their experiment with a more efficient and accurate approach than conventional laboratory techniques. The simulation system 100 interprets the data in the working file 104 to generate a simulation configuration data file 360 (sometimes referred to as a simulation configuration file or a SimConfig file). The file structure of the simulation configuration file 360 includes a set of codified instructions that can be executed by the simulation engine 108 to generate a simulation of the model based on the parameters and conditions specified in the sub-files 320 of the working file 104.

Returning to FIG. 4, the module compiler 106 uses the working file 104 to compile a simulation configuration data file, referred to hereafter as "SimConfig File 104." The compiler 106 functions using the methods and techniques discussed in reference to FIG. 1. As discussed above, the model compilers accesses data from the biochemical database 102 used to generate the codified instructions for the simulation. More specifically, the various specified parameters function as reference terms or pointers that identify relevant pieces of data stored within the biochemical database 102. As a result, based on the specified parameter values of the working file 104, the model compiler 106 retrieves the data corresponding to those terms/pointers from the biochemical database 102, stores the data, and generates the SimConfig file 104 which includes codified instructions to be interpreted by the simulation engine 108.

Figure 5:
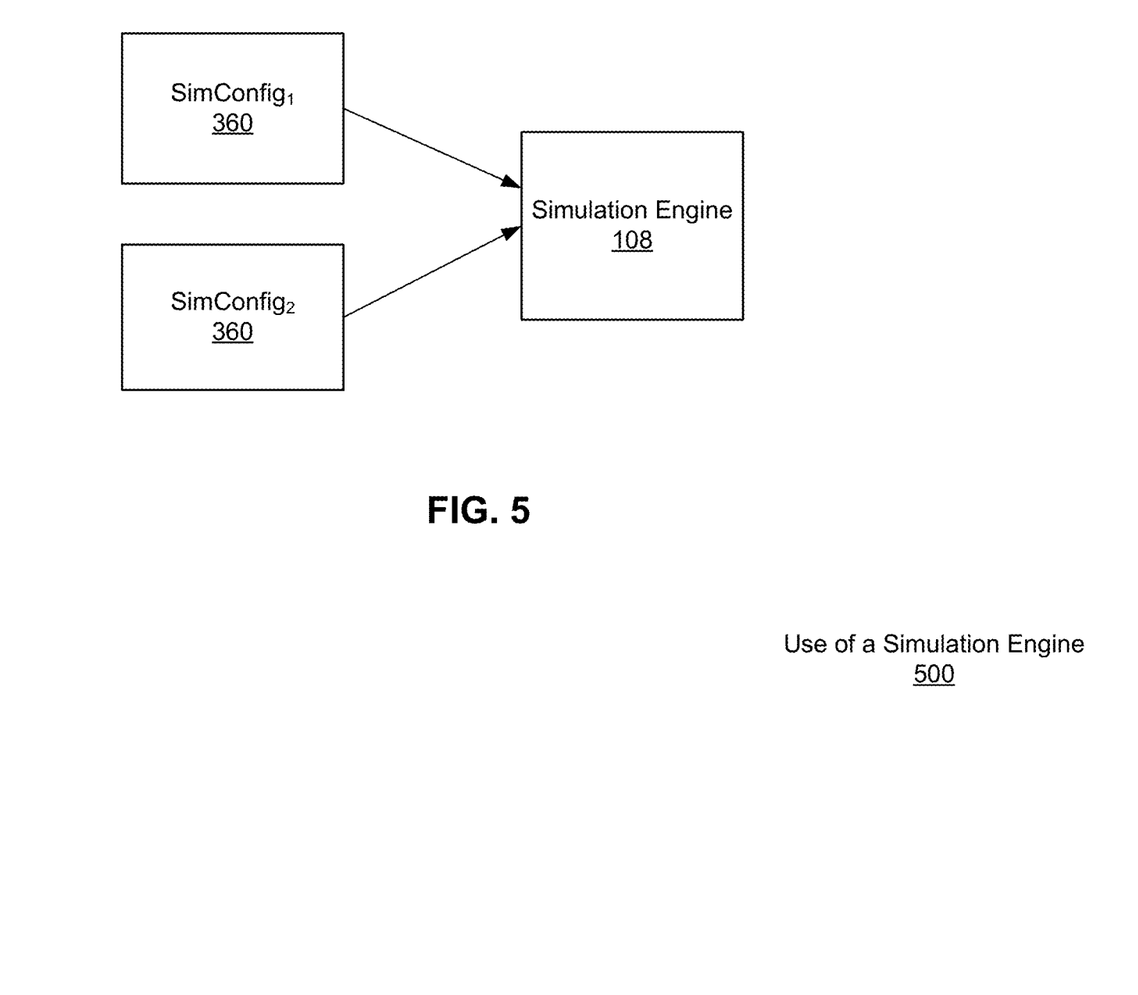
FIG. 5 is a flowchart illustrating the implementation of two different simulation conditions to construct a biological simulation, according to an embodiment.

The SimConfig File 104 is used as input to the simulation engine 108 to perform the calculations required to simulate a biochemical process using the simulation system 100. The simulation engine 108 initializes and executes the simulation using methods and techniques consistent with the description above related to FIG. 1. In some implementations, the simulation engine 108 receives multiple SimConfig files 104, for example SimConfig$_1$ 104*a* and SimConfig$_2$ 104*b* as illustrated in FIG. 5. The multiple SimConfig files 104 may represent different sets of cellular process required to more holistically define a cell or may represent different cells altogether for comparisons between the two simulations.

V. User Interface

V.A Template Builder Interface

Figure 6:
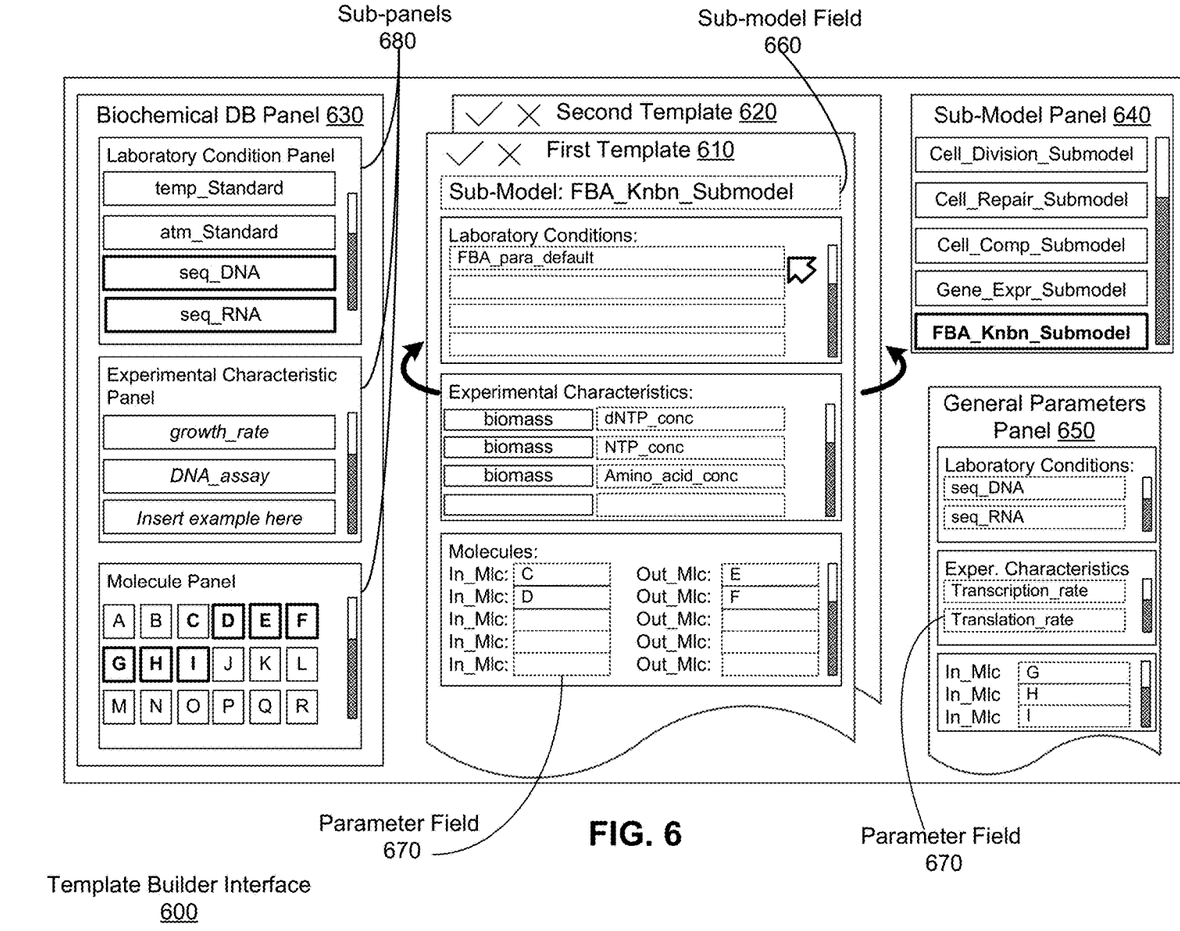
FIG. 6 is an illustration of an example graphical user interface for building a template as displayed on a computer screen, according to an embodiment.

As described earlier in reference to parameter values 350, a graphical user interface for a template display is presented to a user on a computer screen to select and define new characterizations of cellular processes used to perform a simulation. FIG. 6 is an illustration of an example graphical user interface for building a template as displayed on a computer screen. In alternate embodiments, the organization and format of the template builder 600 may differ while maintaining the same functionality as described below. Centrally, the template display 110 presents a list of templates to be designated with sub-model specifications and populated with entries relevant to the sub-model specifications. As illustrated, the list of templates may be presented as scrolling display such that a single template may be viewed and modified by a user at a time, for example the overlaid presentation of first template 610 and second template 620. Examples of user interactions with the graphical user interface 110 include hovering over a graphic element, holding a graphical element, and touching a graphical element one or more times. In alternate implementations, the list of templates may be presented in other cyclic formats or be presented as multiple templates simultaneously The templates 330, as presented by the template builder interface 600, include a sub-model field 660 for a sub-model specification as described above in reference to FIG. 4 and FIG. 4. The template 330 further includes separate sections containing parameter fields 670 for information describing the parameter categories, for example laboratory conditions, experimental characteristics, and process molecules. Upon initial access by the user, the template display 110 may present the user with a blank first template 610 such that a new simulation may be designed. In some implementations, upon specification of a sub-model, certain parameter fields 670 within each of these categories are populated with pre-set entries, for example input molecules C and D and output molecules E and F of the FBA_Knbn_Submodel. Pre-set entries used to define the templates 610 and 620 describe parameters of the cellular process that are: 1) required for the reaction to occur regardless of circumstances surrounding the experiments or 2) present throughout the process regardless of circumstances surrounding the experiments. Pre-set entries may also apply to the laboratory conditions and experimental characteristics of a sub-model, for example default FBA parameters (FBA_para_default) and concentrations of dNTP, NTP, and amino acid (dNTP_conc, NTP_conc, amino_acid_conc), respectively.

Surrounding the templates 610 and 620, the template builder interface 600 displays a biochemical database panel 630 including sub-panels 680 for each of the parameter categories referenced above and sub-model panel 640 detailing a list of sub-model specifications within the sub-model store 340. In alternate implementations, both the biochemical database panel 630 and the sub-model panel 640 are aggregated into a single panel presented by the template display. Each of the sub-panels 680 include a set of selectable entries that may be used to further define the template. Continuing from the above example, sub-model template 610 includes predetermined input molecules C and D and output molecules E and F, however a user may be interested in testing how adding molecules P, Q, and R affect the simulation of the cell. The user interface 110 receives a set of inputs specifying that molecules P, Q, and R be added to the molecules section of the first template 610. Similarly, the template display 110 may receive inputs at the sub-panels 680 of experimental characteristics and laboratory conditions specifying that respective entries be used to populate the template 610, as well. In addition to the selectable molecule entries stored within the molecule panel, the graphical user interface 110 allows the user to assign a concentration of each input or output molecule to further characterize the reactants and products of intracellular reactions. After the parameters of the first template 610 have been used to characterize the specified cellular process, the template display 110 receives an input indicating that a second blank template 620 be presented to the user.

Assignment of parameter values to the blank second template 620 is performed by the simulation system in the same manner outlined in regards to the first template 610. Between the completion of a first template and the specification of a second template, the simulation system 100 refreshes the graphical user interface 110 such that parameters selected from the biochemical database panel 630 and the sub-model panel 640, for example molecules C, D, E, and F, are again made available for selection by the user. In some implementations, the simulation system 100 refreshes the graphical user interface 110 more frequently, for example every time a parameter is assigned to a template. As a result, a single sub-model template 330 may include multiple entries of a single molecule.

In addition to the biochemical database panel 630 and the sub-model panel 640, the graphical user interface 110 also includes a general parameter panel 650 for updating the general parameters as described above in reference to FIG. 4. Similar to the definition of the templates 330, the general parameters panel 650 is divided into sections pertaining to the different parameter categories and each section contains parameter fields that can be populated using the entries within the biochemical database panel 610. Similar to the template 610, entries pre-selected for the sub-model describe conditions that are either unaffected by the other parameters of the process or are required for the process to occur, for example input molecules G, H, and I. Examples of laboratory conditions and experimental characteristics designated as general parameters include, respectively, the DNA or RNA sequence (seq_DNA, seq_RNA) and the transcription or translation rate (transcription_rate, translation_rate).

To populate the parameter fields of the templates 610 and 620 and the general parameters panel 650, the graphical user interface 110 receives inputs from a user to indicating a selection of one or more parameters from the biochemical database panel 630 or sub-model specifications from the sub-model store 640 and an input to indicate the parameter fields with which to populate the selected entries. The graphical user interface 110 may also receive manual updates to the parameter fields in the form of typographical input such as words or numbers. The graphical user interface 110 may assign entries to parameter fields as default parameter values and the template display 110 may update those default parameter values to test specific values in response to an input or instruction from the user.

V.B Working File Builder Interface

As described above, a user may not be interested in designing a simulation requiring completely new characterizations of sub-model templates, but may instead choose to make slight modifications to existing sub-models. As a result, in addition to presenting the template builder interface 600 for designing a simulation, the graphical user interface 110 may present a working file builder interface 700 to a user on a computer screen. The working file builder interface 700 allows a user to select and incorporate existing sub-model templates 330 into a working file 104, as individual sub-files 320, and modify each sub-file directly within the working file 104 To that end, FIG. 7 is an illustration of an example graphical user interface for building a working file as displayed on a computer screen. In alternate embodiments, the organization and format of the working file builder interface 700 may differ while maintaining the same functionality as described below.

Organizationally, the working file builder interface 700 is similar to the template builder interface 600. The working file builder interface 700 also includes a biochemical database panel 630, divided into sub-panels containing options for the parameter categories described above, and a general parameters panel 650 lining the perimeters of the interface 110. Centrally, as illustrated in FIG. 7, in place of the blank templates presented by the template builder interface 600, the working file builder interface 700 presents one or more of the sub-files 320 based on the templates selected for inclusion in the. Each of the sub-files 320a-d are graphically similar in format and informationally identical in content to a template previously designed at the template builder interface 600, such that, with no modifications to the user, the working file 104 may be compiled to simulate an simulation similar, if not identical depending on the combination of sub-files 320, to an simulation previously conducted by the user.

In alternate implementations, because multiple sub-files 320 may be viewed within a single working file 104, each sub-file 320 may presented in a condensed format compared to the format of the sub-model templates 330 as presented by template display 110. The multiple sub-files 320a-d may also be selected as a scrolling display such that a single sub-file 320 may be viewed and modified by a user at a time.

Unlike the template builder interface 600, the working file builder interface 700 does not present a sub-model panel 640 due to the lack of sub-model fields 660 in each of the sub-files 320. More specifically, because each sub-file included in the working file 104 is already based on a sub-model template 330 stored by the simulation system 100, when interacting with the working file builder interface a user would have no need to specify a sub-model from the sub-model panel 640.

Functionally, the working file builder interface 700 responds to similar user interactions as the builder interface 600 to characterize the working file 104 with parameter values consistent with the method described above. Each sub-file 320a-d includes a default set of parameter values assigned during the creation of the respective sub-model template 330. For example, sub-file$_1$ 320a, includes a default set of input molecules C, D, and F and output molecule E, F, K. Sub-file$_1$ 320b includes a default set of input molecules C and D and output molecules P, Q, R, and S. Sub-file$_3$ 320c includes a default set of input molecules A and B and output molecules C and D. Sub-file$_4$ 320d includes a default set of input molecules X, Y, and Z and output A and B. As described above, although not illustrated, the biochemical database panel 630 may also include entries describing specific cellular reactions which can be assigned to each sub-file. Alternatively, those reactions may be implicitly assigned based on the explicit assignment of input and output molecules to a sub-file 320.

Similarly, each sub-file 320 may include a set of default laboratory conditions and experimental characteristics. For example, laboratory conditions for the sub-file$_1$ 320a include default FBA parameters (FBA_para_default), sub-file$_2$ 320b include a standard cell plate (cell_plate_standard), and sub-file$_4$ 320d include concentrations of RNA polymerase and a translation agent (RNA_poly_conc, trans_agent_conc). Each sub-file 320 may also include a set of default experimental characteristics, for example dNTP and NTP concentrations (dNTP_conc, NTP_conc), an enzyme concentration (enzyme_conc), the production rate of DNA (DNA_prod_rate), and rates of transcription and translation (transcription_rate, translation_rate).

To modify the sub-files 320 beyond their default parameter values, the simulation system 100 assigns entries from each sub-panel of the biochemical database panel 630 to parameter fields describing laboratory conditions, experimental characteristics, or molecules of each sub-file 320. In addition to assigning parameter values, each sub-file 320 allows a user to modify or delete the one or more default parameter values based on considerations to the current simulation being simulated.

Contextually, the working file builder interface presents the user with insight about cellular processes in regards to the full cell-model. As described in reference to the full cell model 200, the output molecules of some cellular processes may be used as input molecules to upstream cellular processes. By specifying input and output molecules for each sub-file, the graphical user interface 110 is able to graphically design and represent the upstream and downstream relationships of various cellular processes. For example, because molecules A and B are output molecules in sub-file$_4$ 420d and input molecules in sub-file$_3$ 420c, the simulation system deduces that the processes associated with gene expression are downstream of processes associated with cell replication. Such insight is unique to the design of a simulation environment rather than conventional wet lab techniques.

VI. Benefits

Compared to convention computer simulation systems, the simulation system 100 generates and highly specific and detailed data structures providing users allowing users to a greater amount of flexibility to customize simulations of experiments. Each working file 104 and simulation configuration file 360 include several layers of additional detail that conventional systems lack, for example multiple cellular processes, environmental conditions, laboratory conditions, and molecules both unique to each process and generally describing the cell.

Storage of these specified data structures provides a more efficient means for reproducing data from previously designed simulations or for expanding on the results found in a previously designed experiment. Rather than repeatedly designing a simulation from first principles, a user may recall and make specific modifications to sub-model templates from previously performed simulations. Additionally, by codifying the conditions and considerations used to design simulations, users are able to more efficiently and accurately design simulations with a greater degree of specificity and flexibility than conventional systems.

From a diagnostic perspective, the simulation system facilitates the ability for scientists to predict the effects of changed states on cells and to develop new targets and drugs for affecting those cells. Further, these techniques provide a rapid and inexpensive means for identifying and evaluating those new targets and drugs by reducing the amount of in vivo research needed to evaluate those targets and drugs.

VII. Additional Considerations

A number of embodiments have been described. Nevertheless, it will be understood that various modifications may be made without departing from the spirit and scope of the invention.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
  accessing, with a computer, a knowledge base data structure comprising a plurality of entries, the entries representing distinct molecules and entries representing distinct chemical reactions;
  accessing, with the computer, a set of templates, each template including a sub-model program specification and a set of sub-model parameters corresponding to a set of sub-model parameter fields, wherein the accessed set of templates includes a shared sub-model program specification, each template of the accessed set receiving different parameter values for assignment to the sub-model parameter fields;

providing, through the computer, a graphical user interface for display on a computer screen, the graphical user interface providing for viewing and selection of at least one of: one or more of the templates, and one or more of the entries of the knowledge base data structure;

receiving, at the computer, a set of input selections specifying a plurality of the templates of the set for inclusion in a simulation and assignment for a plurality of entries from the knowledge base data structure to the specified templates, wherein the knowledge base data structure comprises a representation of a reaction network containing the plurality of entries for assignment to the selected templates; and executing, by the computer, a compiler to generate a simulation configuration data file based on the set of input selections, the simulation configuration data file comprising computer code that is executed by a simulation engine.

2. The method of claim 1, wherein the sub-model parameters include one or more of the following:
at least one laboratory condition, further comprising:
an environmental temperature;
a type of plating;
an atmospheric composition;
a transcription agent;
a concentration of the transcription agent;
a translation agent; and
a concentration of the translation agent.

3. The method of claim 1, wherein the sub-model parameters include one or more of the following:
at least one experimental characteristic, further comprising:
a quantity to be analyzed; and
a method for analyzing the quantity.

4. The method of claim 3, wherein a quantity to be analyzed comprises:
a concentration of deoxynucleoside triphosphate;
a concentration of nucleoside triphosphate;
a concentration of one or more amino acids;
a rate of transcription;
a rate of translation; and
a production rate of DNA.

5. The method of claim 1, wherein the sub-model parameters include one or more of the following:
at least one molecule, further comprising:
one or more input molecules;
one or more output molecules; and
one or more reaction networks relating the input molecules to the output molecules.

6. The method of claim 1, further comprising accessing one or more general parameters describing one or more features of a cell independent of the sub-model programs associated with the set of templates, the general parameters comprising:
one or more general laboratory conditions;
one or more general experimental characteristics; and
one or more molecules within the cell.

7. The method of claim 6, wherein general parameters include one or more of the following:
information to identify the organism, further comprising:
a DNA sequence for the organism;
one or more edits to the DNA sequence for the organism;
a RNA sequence for the organism; and
one or more edits to the RNA sequence for the organism.

8. The method of claim 1, wherein, for a particular template of the set of templates, the sub-model program specification included in the particular template specifies a cellular process represented by the particular template.

9. The method of claim 1, further comprising:
generating a sub-file, the sub-file representing a template with sub-model parameters and a sub-model program specification for a single process within a cell.

10. The method of claim 1, further comprising:
generating a working data file, the working data file comprising:
a plurality of sub-files to simultaneously describing multiple processes within a cell, each sub-file representing a sub-model program unique from other sub-files of the plurality; and
a plurality of general parameters independent of the plurality of sub-files.

11. The method of claim 10, wherein the working data file comprises computer code that is being executed by a simulation engine.

12. The method of claim 1, further comprising:
retrieving, at the computer, the simulation configuration data file generated by the compiler; and
executing, by the computer, a simulation engine to generate a simulated model of a cell based on the retrieved simulation configuration data file generated by the compiler.

13. The method of claim 1, further comprising:
retrieving, by the computer, a plurality of simulation configuration data files generated by the compiler; and
executing, by the computer, a simulation engine to generate a simulated model of a cell based on the plurality of simulation configuration data files generated by the compiler, each simulation configuration data file of the plurality describing a different combination of entries, parameter values, and templates.

14. The method of claim 1, wherein the graphical user interface provided for display on the computer screen comprises:
a first graphical element identifying the plurality of entries stored within the knowledge base, the sub-model parameters separated into a plurality of parameter categories comprising one or more of the following:
a set of laboratory conditions;
a set of environmental characteristics;
a set of molecules; and
a set of reactions.

15. The method of claim 1, wherein the graphical user interface provided for display on the computer screen comprises:
a second graphical element identifying the plurality of general parameters, the plurality of general parameters separated into a plurality of parameter categories comprising one or more of the following:
a set of laboratory conditions;
a set of environmental characteristics;
a set of molecules; and
a set of reactions.

16. The method of claim 1, wherein the graphical user interface provided for display on the computer screen further comprises:
a third graphical element identifying a plurality of sub-model program specifications.

17. The method of claim 1, wherein the graphical user interface provided for display on the computer screen further comprises:

a plurality of initial sub-model templates, each sub-model template of the plurality comprising:
a plurality of available parameters fields to be populated by one or more entries within the knowledge base; and
an available field to be populated with a sub-model program specification.

18. The method of claim 1, wherein the graphical user interface provided for display on the computer screen further comprises:
a plurality of sub-files with populated parameter fields, the parameter fields to be adjusted in response to a user interaction with the graphical user interface.

19. The method of claim 1, wherein providing the graphical user interface for display on a computer screen further comprises:
responsive to a user interaction with the graphical user interface, identifying an entry from the knowledge base to be included in a sub-file; and
identifying an available parameter field within the sub-file for assignment of the identified entry.

20. The method of claim 19, wherein user interaction comprises one or more of the following:
hovering over a graphical element;
holding a graphical element; and
touching a graphical element one or more times.

21. The method of claim 1, wherein providing the graphical user interface for display further comprises:
reconfiguring a layout of the graphical user interface in response to one or more of the following:
an assignment of a sub-model program specification to a field, the reconfiguration identifying parameter values associated with a sub-model template;
a selection of an entry from the knowledge base, the reconfiguration allowing the selected entry to be selected a plurality of times;
an assignment of an entry to a parameter field; and
an insertion or deletion of a parameter value from a parameter field.

22. A non-transitory computer readable storage medium storing instructions encoded thereon that, when executed by a processor, cause the processor to perform the steps comprising:
accessing, with a computer, a knowledge base data structure comprising a plurality of entries, the entries representing distinct molecules and entries representing distinct chemical reactions;
accessing, with the computer, a set of templates, each template including a sub-model program specification and a set of sub-model parameters corresponding to a set of sub-model parameter fields, wherein the accessed set of templates includes a shared sub-model program specification, each template of the accessed set receiving different parameter values for assignment to the sub-model parameter fields;
providing, through the computer, a graphical user interface for display on a computer screen, the graphical user interface providing for viewing and selection of at least one of: one or more of the templates, and one or more of the entries of the knowledge base data structure;
receiving, at the computer, a set of input selections specifying a plurality of the templates of the set for inclusion in a simulation and assignment for a plurality of entries from the knowledge base data structure to the specified templates, wherein the knowledge base data structure comprises a representation of a reaction network containing the plurality of entries for assignment to the selected templates; and
executing, by the computer, a compiler to generate a simulation configuration data file based on the set of input selections, the simulation configuration data file comprising computer code that is executed by a simulation engine.

23. A system comprising:
a processor; and
a non-transitory computer readable storage medium storing instructions encoded thereon that, when executed by a processor, cause the processor to perform the steps comprising:
accessing, with a computer, a knowledge base data structure comprising a plurality of entries, the entries representing distinct molecules and entries representing distinct chemical reactions;
accessing, with the computer, a set of templates, each template including a sub-model program specification and a set of sub-model parameters for the sub-model program corresponding to a set of sub-model parameter fields, wherein the accessed set of templates includes a shared sub-model program specification, each template of the accessed set receiving different parameter values for assignment to the sub-model parameter fields;
providing, through the computer, a graphical user interface for display on a computer screen, the graphical user interface providing for viewing and selection of at least one of: one or more of the templates, and one or more of the entries of the knowledge base data structure;
receiving, at the computer, a set of input selections specifying a plurality of the templates of the set for inclusion in a simulation and assignment for a plurality of entries from the knowledge base data structure to the specified templates, wherein the knowledge base data structure comprises a representation of a reaction network containing the plurality of entries for assignment to the selected templates; and
executing, by the computer, a compiler to generate a simulation configuration data file based on the set of input selections, the simulation configuration data file comprising computer code that is executed by a simulation engine.

* * * * *